(12) United States Patent
Heraty et al.

(10) Patent No.: US 9,149,377 B2
(45) Date of Patent: Oct. 6, 2015

(54) STENT SUITABLE FOR DEPLOYMENT IN A BLOOD VESSEL

(75) Inventors: Kevin Heraty, Castlebar (IE); Liam Mullins, Athlone (IE)

(73) Assignee: Veryan Medical Ltd., Oxford (GB)

( * ) Notice: Subject to any disclaimer, the term of this patent is extended or adjusted under 35 U.S.C. 154(b) by 736 days.

(21) Appl. No.: 12/249,389

(22) Filed: Oct. 10, 2008

(65) Prior Publication Data

US 2010/0094391 A1    Apr. 15, 2010

(51) Int. Cl.
| | | |
|---|---|---|
| A61F 2/06 | (2013.01) | |
| A61F 2/915 | (2013.01) | |
| A61F 2/91 | (2013.01) | |
| A61F 2/89 | (2013.01) | |
| A61F 2/82 | (2013.01) | |

(52) U.S. Cl.
CPC . *A61F 2/915* (2013.01); *A61F 2/89* (2013.01); *A61F 2/91* (2013.01); *A61F 2002/826* (2013.01); *A61F 2250/0018* (2013.01); *A61F 2250/0036* (2013.01); *A61F 2250/0039* (2013.01)

(58) Field of Classification Search
CPC ... A61F 2/82; A61F 2/86; A61F 2002/91508; A61F 2002/91516
USPC ............. 623/1.11, 1.15, 1.16, 1.22, 1.17; 606/198
See application file for complete search history.

(56) References Cited

U.S. PATENT DOCUMENTS

| | | |
|---|---|---|
| 4,531,933 A | 7/1985 | Norton et al. |
| 4,681,570 A | 7/1987 | Dalton |
| 4,813,925 A | 3/1989 | Anderson, Jr. et al. |

(Continued)

FOREIGN PATENT DOCUMENTS

| | | |
|---|---|---|
| EP | 0 800 801 A1 | 10/1997 |
| EP | 1 279 382 A1 | 1/2003 |

(Continued)

OTHER PUBLICATIONS

European Search Report corresponding to EP 08 25 3318, Jan. 16, 2009 (English Text).

(Continued)

*Primary Examiner* — Katrina Stransky
(74) *Attorney, Agent, or Firm* — Fay Sharpe LLP

(57) ABSTRACT

A stent (1) comprises a central section (2), a first intermediate section (3), a first end section (4), a second intermediate section (5), and a second end section (6). The stent (1) is movable between a collapsed delivery configuration and an expanded deployment configuration. In the delivery configuration the central section (2), the first intermediate section (3), the first end section (4), the second intermediate section (5), and the second end section (6) are all cylindrically shaped. In the deployment configuration the central section (2) is helically shaped, while the first end section (4) and the second end section (6) remain cylindrically shaped. Each intermediate section (3, 5) acts as a blended region to provide a smooth transition from the helical shape of the central section (2) to the cylindrical shape of the unstented blood vessel. The radial stiffness of the stent (1) varies gradually along part of the length of the stent (1). The radial stiffness of the end region of the stent (1) is less than the radial stiffness of a first region located further in from the end of the stent (1). The variation in radial stiffness reduces the area of blood vessel wall which has low wall shear stress, reduces the possibility of recirculation, and reduces the risk of neointimal hyperplasia.

18 Claims, 9 Drawing Sheets

(56) References Cited

U.S. PATENT DOCUMENTS

| | | |
|---|---|---|
| 5,749,919 A | 5/1998 | Blanc |
| 5,938,697 A | 8/1999 | Killion et al. |
| 5,984,965 A | 11/1999 | Knapp et al. |
| 6,027,526 A | 2/2000 | Limon et al. |
| 6,673,102 B1 * | 1/2004 | Vonesh et al. ............... 623/1.13 |
| 6,685,738 B2 * | 2/2004 | Chouinard et al. .......... 623/1.15 |
| 7,326,240 B1 | 2/2008 | Caro et al. |
| 2001/0031981 A1 | 10/2001 | Evans et al. |
| 2001/0049549 A1 | 12/2001 | Boylan et al. |
| 2002/0095206 A1 | 7/2002 | Addonizio et al. |
| 2003/0135265 A1 | 7/2003 | Stinson |
| 2003/0208256 A1 | 11/2003 | DiMatteo et al. |
| 2004/0044400 A2 | 3/2004 | Cheng et al. |
| 2004/0087886 A1 | 5/2004 | Gellman |
| 2004/0088043 A1 * | 5/2004 | Klein ........................... 623/1.16 |
| 2004/0133266 A1 | 7/2004 | Clerc et al. |
| 2004/0193254 A1 | 9/2004 | Greenberg et al. |
| 2004/0243216 A1 | 12/2004 | Gregorich |
| 2006/0015173 A1 | 1/2006 | Clifford et al. |
| 2006/0184232 A1 * | 8/2006 | Gianotti et al. .............. 623/1.15 |
| 2006/0247759 A1 * | 11/2006 | Burpee et al. ................ 623/1.15 |
| 2006/0265051 A1 * | 11/2006 | Caro et al. ................... 623/1.17 |
| 2007/0129786 A1 | 6/2007 | Beach et al. |
| 2007/0156078 A1 | 7/2007 | Caro et al. |
| 2007/0185563 A1 * | 8/2007 | Zarbatany et al. ........... 623/1.15 |
| 2007/0191927 A1 | 8/2007 | Bowe et al. |
| 2007/0293932 A1 | 12/2007 | Zilla et al. |
| 2008/0262599 A1 | 10/2008 | Caro et al. |
| 2012/0016460 A1 | 1/2012 | Heraty et al. |

FOREIGN PATENT DOCUMENTS

| | | |
|---|---|---|
| GB | 2 418 362 A | 3/2006 |
| JP | 2006-520630 | 9/2006 |
| JP | 2008-513171 | 5/2008 |
| WO | WO 98/22159 | 5/1998 |
| WO | WO 00/28922 | 5/2000 |
| WO | WO 00/32241 | 6/2000 |
| WO | WO 00/69366 | 11/2000 |
| WO | WO 03/057079 A1 | 7/2003 |
| WO | WO 2004/082520 A2 | 9/2004 |
| WO | WO 2004/082533 | 9/2004 |
| WO | WO 2004/082533 A1 | 9/2004 |
| WO | WO 2006/032902 | 3/2006 |
| WO | WO 2007/131798 | 11/2007 |

OTHER PUBLICATIONS

International Search Report of International Application No. PCT/GB2009/002437 dated Feb. 15, 2010 (English Text).

* cited by examiner

STENT SUITABLE FOR DEPLOYMENT IN A BLOOD VESSEL

INTRODUCTION

This invention relates to a stent suitable for deployment in a blood vessel to support at least part of an internal wall of the blood vessel.

STATEMENT OF INVENTION

According to the invention there is provided a stent suitable for deployment in a blood vessel to support at least part of an internal wall of the blood vessel, the stent being movable between a delivery configuration and a deployment configuration.

In one embodiment of the invention the stent comprises a first region and a second region, the radial stiffness of the first region being greater than the radial stiffness of the second region. This arrangement reduces the area of the internal wall of the blood vessel which has low wall shear stress, reduces the possibility of recirculation, and reduces the risk of neointimal hyperplasia. Wall shear stress is generated on the internal wall of a blood vessel by flow adjacent to the wall. Levels of mean wall shear stress below 0.4 Pa have been shown to have a pathogenic effect on endothelial cells which cover the inner surface of the arteries. Higher levels of wall shear stress, for example greater than 1.5 Pa, have been associated with a reduction in levels of in-stent restenosis. Preferably the radial stiffness varies gradually from the first region towards the second region. Ideally the second region is closer to an end of the stent than the first region. Most preferably the second region is located at an end of the stent.

In one case the stent comprises a plurality of annular elements. Preferably the longitudinal dimension of an annular element in the first region is less than the longitudinal dimension of an annular element in the second region. In this manner the radial stiffness is reduced by increasing the longitudinal dimension of the annular element. Ideally the longitudinal dimension of the annular element in the second region is between 1% and 90% greater than the longitudinal dimension of the annular element in the first region. Most preferably the longitudinal dimension of the annular element in the second region is between 1% and 75% greater than the longitudinal dimension of the annular element in the first region. The longitudinal dimension of the annular element in the second region may be approximately 40% greater than the longitudinal dimension of the annular element in the first region. The thickness of the annular element in the first region may be greater than the thickness of the annular element in the second region. In this manner the radial stiffness is reduced by reducing the thickness of the annular element. In this specification, the term 'thickness' will be understood to mean the dimension in the radial direction.

The stent may comprise one or more connecting elements to connect a first annular element to a second annular element. Preferably the connecting element extends from the first annular element to the second annular element in a non-straight configuration. Ideally the connecting element extends from the first annular element to the second annular element in a substantially curved configuration.

The annular element may comprise a plurality of interconnected strut elements. Preferably the length of the strut element in the first region is less than the length of the strut element in the second region. In this manner the radial stiffness is reduced by increasing the length of the strut element. Ideally the length of the strut element in the second region is between 1% and 90% greater than the length of the strut element in the first region. Most preferably the length of the strut element in the second region is between 1% and 75% greater than the length of the strut element in the first region. The length of the strut element in the second region may be approximately 40% greater than the length of the strut element in the first region. The width of the strut element in the first region may be greater than the width of the strut element in the second region. In this manner the radial stiffness is reduced by reducing the width of the strut element. Preferably the width of the strut element in the first region is between 2% and 50% greater than the width of the strut element in the second region. Ideally the width of the strut element in the first region is between 10% and 30% greater than the width of the strut element in the second region. The width of the strut element in the first region is approximately 20% greater than the width of the strut element in the second region. The thickness of the strut element in the first region may be greater than the thickness of the strut element in the second region. In this manner the radial stiffness is reduced by reducing the thickness of the strut element.

In one embodiment a first strut element is connected to a second strut element at a connection point. Preferably the connecting element is connected to the annular element at the connection point.

The thickness of the stent wall may be greater in the first region than in the second region. For example, where the stent comprises annular elements, an annular element in the first region may have a greater thickness than an annular element in the second region. Where the annular elements comprise interconnected strut elements, the strut elements in the first region may have a greater thickness than an annular element in the second region.

In one case in the deployment configuration the longitudinal axis of at least a section of the stent is curved in three-dimensional space. When the stent is deployed in the blood vessel, the stent exerts force on the blood vessel causing at least part of the longitudinal axis of the blood vessel to curve in three-dimensional space. Blood flowing through the three-dimensional curved part of the blood vessel then undergoes a swirling action. The swirling flow of blood has been found to minimise thrombosis and platelet adhesion, and to minimise or prevent coverage of the stent by ingrowth of intima. The flow pattern in the blood vessel including the swirling pattern induced by the non-planar geometry of the blood vessel operates to inhibit the development of vascular diseases such as thrombosis/atherosclerosis and intimal hyperplasia. In the deployment configuration the three-dimensional curved section may be substantially helically shaped. In the deployment configuration the three-dimensional curved section may be substantially spiral shaped. In the delivery configuration the longitudinal axis of the three-dimensional curved section may be substantially straight. Ideally in the delivery configuration the three-dimensional curved section is substantially cylindrically shaped. The cylindrical shape provides a low-profile for ease of delivery.

In the deployment configuration the longitudinal axis of at least a section of the stent may be substantially straight. Most preferably in the deployment configuration the straight section is substantially cylindrically shaped.

At least a section of the stent may have a helical angle which varies along the length of the section. This arrangement reduces the area of the internal wall of the blood vessel which has low wall shear stress, reduces the possibility of recirculation, and reduces the risk of neointimal hyperplasia. Preferably the helical angle varies gradually along the length of the varying helical angle section. The helical angle at one end of the varying helical angle section may be in the range of from 5° to 60°. Preferably the helical angle at one end of the varying helical angle section is in the range of from 15° to 45°. Ideally the helical angle at one end of the varying helical angle section is approximately 30°. The helical angle at the other end of the varying helical angle section may be approximately 0°. The helical angles discussed herein are those when the stent is in its deployment configuration but not constrained by being in a vessel. When the stent is in a vessel there may be a tendency for it to be straightened out and hence a reduction in the helix angle.

The stent may comprise a first end section and a second end section. Preferably the longitudinal axis of the first end section is substantially parallel to the longitudinal axis of the second end section. Ideally the longitudinal axis of the first end section is substantially co-linear with the longitudinal axis of the second end section.

The invention provides in one case a stent having varying radial stiffness. The radial stiffness may be less at one end or both ends. The stiffness may be reduced by reducing the stent wall thickness, for example the strut thickness. The radial stiffness may be tapered towards the end of the stent. In this manner arterial injury at the stent ends may be reduced or avoided. The invention may also help to regulate wall shear stress at the inlet and outlet which may occur due to a sudden change in cross sectional area.

BRIEF DESCRIPTION OF THE DRAWINGS

The invention will be more clearly understood from the following description of some embodiments thereof, given by way of example only, with reference to the accompanying drawings, in which.

DETAILED DESCRIPTION

Figure 1:
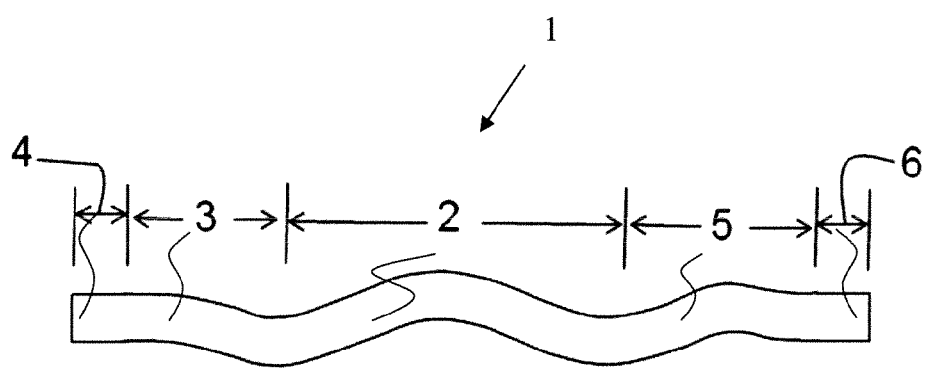
FIG. 1 is a side view of a stent according to the invention in a deployment configuration.

Referring to the drawings, and initially to FIG. 1 thereof, there is illustrated a stent 1 according to the invention. The stent 1 is suitable for deployment in a blood vessel to support at least part of an internal wall of the blood vessel.

The stent 1 comprises a central section 2, a first intermediate section 3, a first end section 4, a second intermediate section 5, and a second end section 6. The first intermediate section 3 connects the central section 2 and the first end section 4. Similarly the second intermediate section 5 connects the central section 2 and the second end section 6.

The stent 1 is movable between a collapsed delivery configuration and an expanded deployment configuration (FIG. 1). In the delivery configuration the longitudinal axis of the central section 2 is substantially straight. In particular in the delivery configuration the central section 2, the first intermediate section 3, the first end section 4, the second intermediate section 5, and the second end section 6 are all cylindrically shaped. In the deployment configuration the longitudinal axis of the central section 2 is curved in three-dimensional space. In the deployment configuration the longitudinal axis of the first end section 4 and the longitudinal axis of the second end section 6 are both substantially straight. In particular in the deployment configuration the central section 2 is helically shaped, while the first end section 4 and the second end section 6 remain cylindrically shaped (FIG. 1).

In this case the stent 1 is of a shape memory material such as Nitinol. It will be appreciated that the stent 1 may alternatively be of other materials, such as 316 L stainless steel.

In the delivery configuration and in the deployment configuration, the longitudinal axis of the first end section 4 is parallel to and co-linear with the longitudinal axis of the second end section 6, as illustrated in FIG. 1.

FIG. 1 illustrates the blended regions 3, 5, and the helical region 2. The stent and vessel centrelines are co-linear.

In an alternative arrangement, the longitudinal axis of the first end section may be parallel to and offset from the longitudinal axis of the second end section.

The first intermediate section 3 has a helical angle α which varies gradually along the length of the first intermediate section 3 from the central section 2 towards the first end section 4. Similarly the second intermediate section 5 has a helical angle α which varies gradually along the length of the second intermediate section 5 from the central section 2 towards the second end section 6. Each intermediate section 3, 5 acts as a blended region to provide a smooth transition from the helical shape of the central section 2 to the cylindrical shape of the unstented blood vessel.

The helical angle α at the central section 2 may be in the range of from 5° to 60°, preferably in the range of from 15° to 45°, and in this case is approximately 30°.

Figure 2:
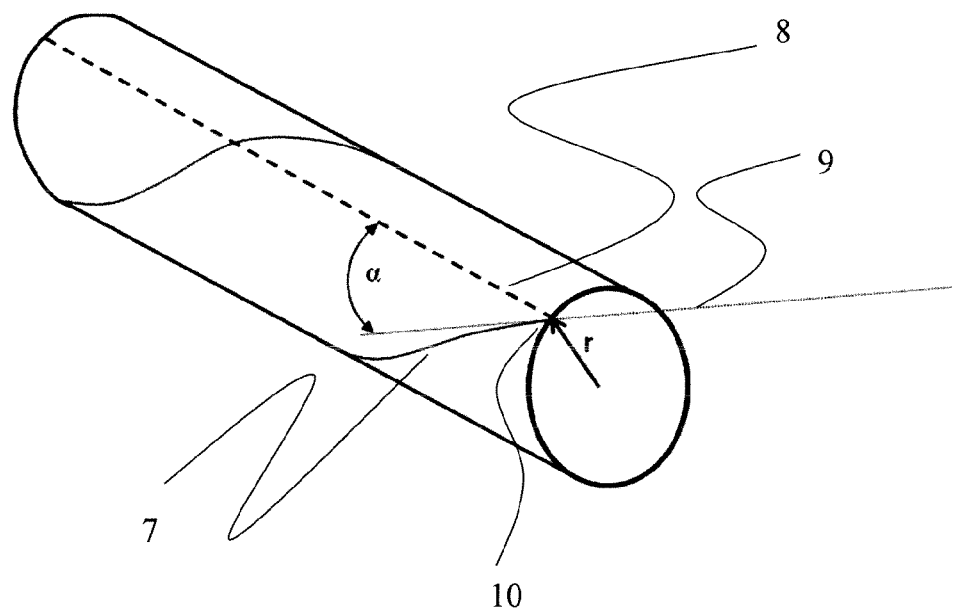
FIG. 2 is a schematic isometric view to illustrate definition of a helical angle.

The definition of the helical angle α is illustrated in FIG. 2. Consider the helical line 7 shown in FIG. 2. Every helical line may be described by the radius r of the cylinder it lies on and the helical angle α. The helical angle α is described as the angle subtended by a parallel line 8 and a tangential line 9. The parallel line 8 is a line lying on the cylinder and parallel to the centreline of the cylinder. The tangential line 9 is a line tangential to the helical line 7 at the point of intersection 10 of the parallel line 8 and the helical line 7.

In this case the helical angle α varies from approximately 30° at the central section 2 to approximately 0° at the end sections 4, 6. The length of each intermediate section 3, 5 is approximately 22 mm in this case.

The stent diameter may be in range of from 2 mm to 20 mm. In this case the stent diameter is approximately 6 mm.

It will be appreciated that the intermediate sections 3, 5 may have a range of helical angles and may have a range of diameters.

The definition of the helical line 7 defines the centreline path of the final forming tool geometry and therefore has a significant effect on the stent shape. The stent forming tool has a helical section towards its centre and blended regions at the proximal and distal ends. The centreline of the forming tool has a helical and blended region.

In this case the forming tool has a constant diameter and a constant cross-section over its length.

After deployment of the stent 1, the stent 1 adjusts the geometry of the blood vessel into a helical pattern. The curvature of the intermediate sections 3, 5 is matched to that of the vessel centreline, as shown in FIG. 1.

FIG. 1 illustrates the stent 1 co-linear with the blood vessel. The blended regions 3, 5 match the rate of change of centreline curvature from the helical region 2 to the straight blood vessel.

Figure 5:
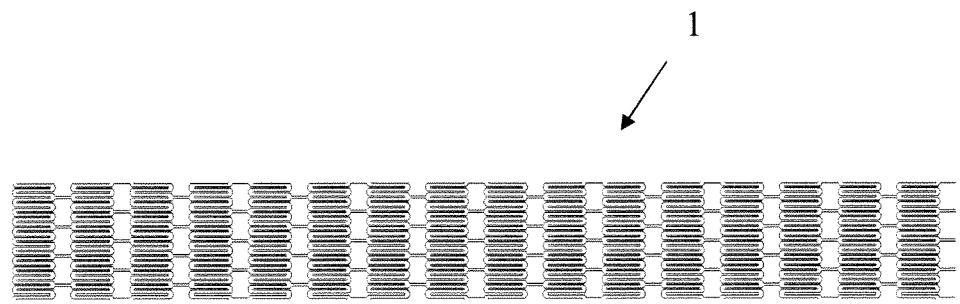
FIG. 5 is a side view of part of the stent of FIG. 1 in a delivery configuration.

FIG. 5 illustrates the stent 1 in the collapsed state.

Figure 6:
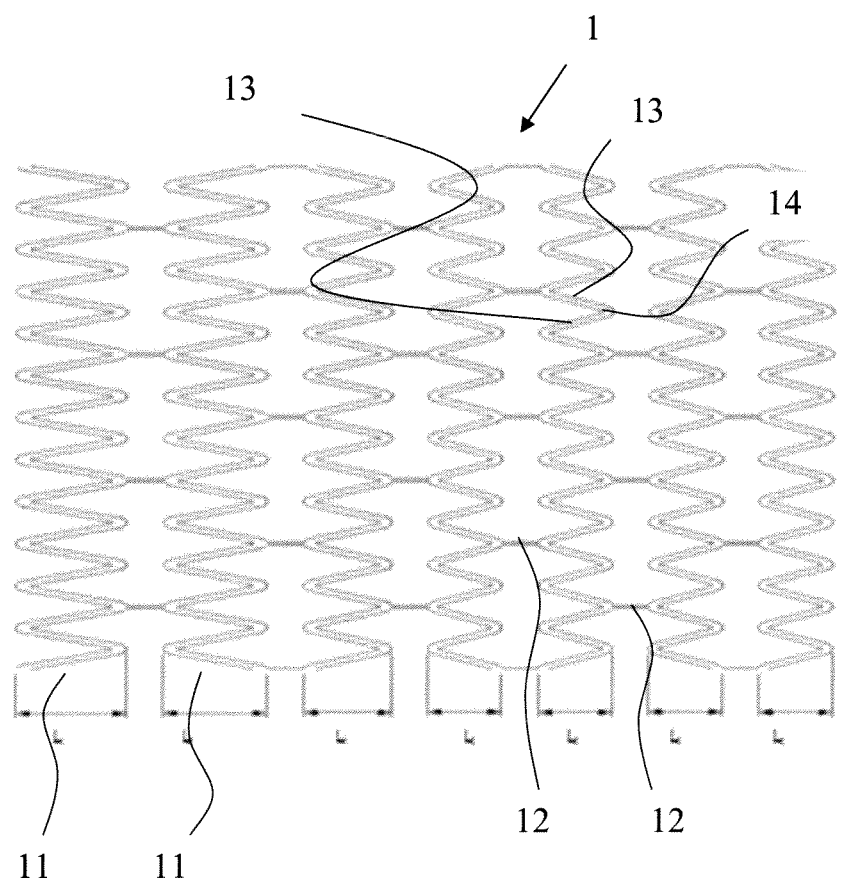
FIG. 6 is a side view of part of the stent of FIG. 1 in the deployment configuration.

As illustrated in FIG. 6, the stent 1 comprises a plurality of annular elements 11, and a plurality of connecting elements 12 to connect adjacent annular elements 11.

Each annular element 11 extends around the circumference of the stent 1. Each annular element 11 comprises a plurality of interconnected strut elements 13. Adjacent strut elements 13 are connected together at connection points 14.

Each connecting element 12 may extend from a first annular element 11 to a second annular element 11 in a straight configuration, or in a curved 'Z' shaped configuration. Each connecting element 12 is connected to the annular element 11 at a connection point 14.

It will be appreciated that the stent of the invention may have a variety of possible patterns. For example the connecting element 12 may extend from a first annular element 11 to a second annular element 11 in a curved 'S' shaped configuration. The connecting element 12 between the penultimate annular element 11 and the final annular element 11 may comprise a 'V' shaped portion.

Figure 8:
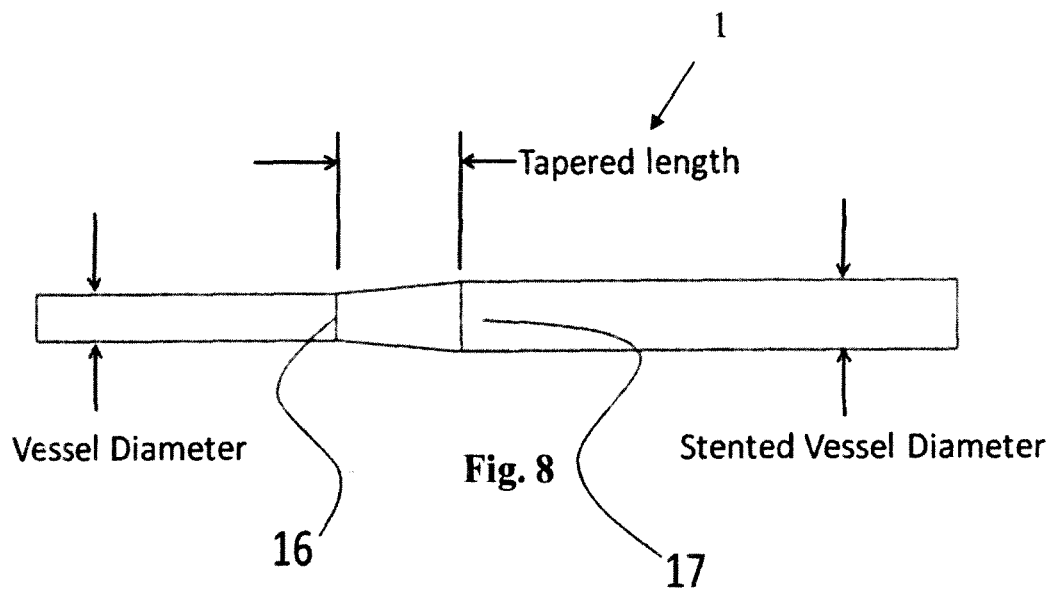
FIG. 8 is a side view of part of the stent of FIG. 1 in the deployment configuration.

The radial stiffness of the stent 1 varies gradually along part of the length of the stent 1, as illustrated in FIG. 8. In particular the radial stiffness of the end region 16 of the stent 1 is less than the radial stiffness of a first region 17 located further in from the end of the stent 1. The radial stiffness of the stent 1 varies gradually from the first region 17 towards the end region 16.

In this case the first region 17 is located approximately 8 mm from the end region 16.

The variation in radial stiffness may be achieved by a variety of different means.

For example the longitudinal dimension of the annular element 11 in the first region 17 may be less than the longitudinal dimension of the annular element 11 in the end region 16, as illustrated in FIG. 6. The longitudinal dimension of the annular element 11 in the end region 16 may be between 1% and 90% greater than the longitudinal dimension of the annular element 11 in the first region 17, preferably between 1% and 75% greater, and in this case is approximately 40% greater. Similarly the length of the strut elements 13 in the first region 17 may be less than the length of the strut elements 13 in the end region 16. The length of the strut elements 13 in the end region 16 may be between 1% and 90% greater than the length of the strut elements 13 in the first region 17, preferably between 1% and 75% greater, and in this case is approximately 40% greater.

FIG. 6 illustrates the variation in radial stiffness using strut length.

Figure 7:
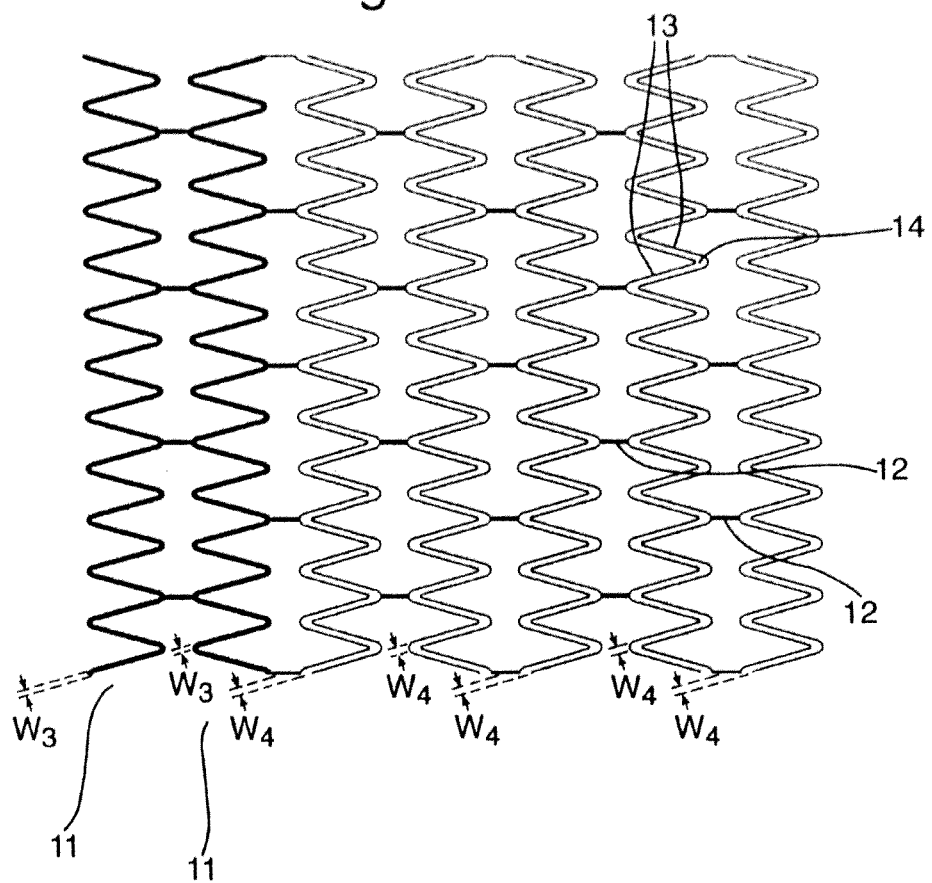
FIG. 7 is a side view of part of another stent according to the invention in the deployment configuration.

As another example the width of the strut elements 13 in the first region 17 may be greater than the width of the strut elements 13 in the end region 16, as illustrated in FIG. 7. The width of the strut elements 13 in the first region 17 may be between 2% and 50% greater than the width of the strut elements 13 in the end region 16, preferably between 10% and 30% greater, and in this case is approximately 20% greater.

FIG. 7 illustrates the variation in radial stiffness using strut width.

As another example the thickness of the annular element 11 in the first region 17 may be greater than the thickness of the annular element 11 in the end region 16. Similarly the thickness of the strut elements 13 in the first region 17 may be greater than the thickness of the strut elements 13 in the end region 16.

Figure 3:
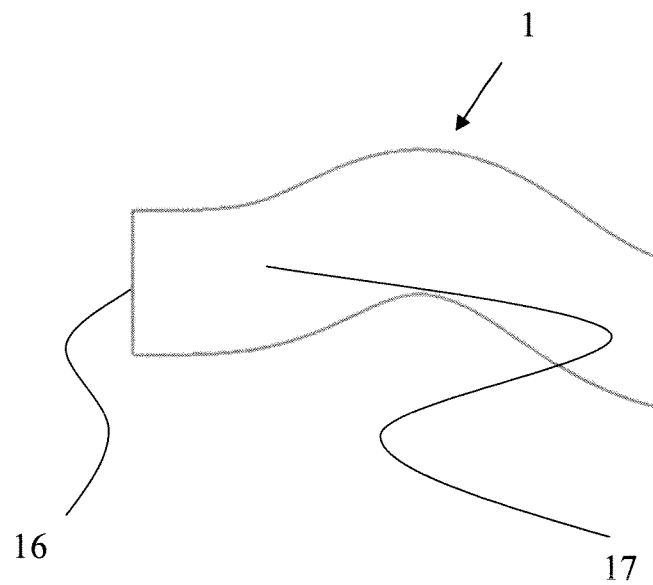
FIG. 3 is a side view of part of the stent of FIG. 1 in the deployment configuration before deployment in a blood vessel.
Figure 4:
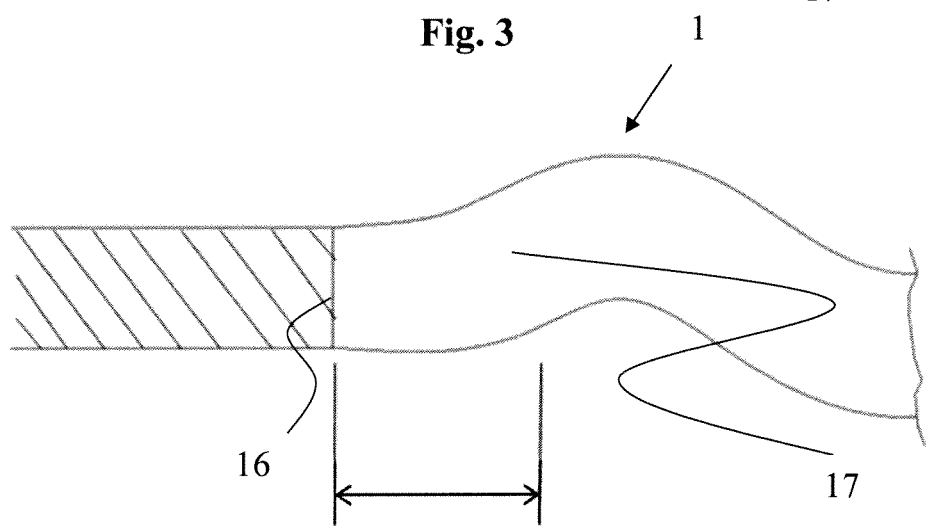
FIG. 4 is a side view of the part of the stent of FIG. 3 in the deployment configuration after deployment in a blood vessel.

Prior to delivery when the stent 1 is outside of the blood vessel, the stent 1 has a constant diameter from the first region 17 to the end region 16, as illustrated in FIG. 3. After deployment of the stent 1 in the blood vessel, the stent 1 has a tapered configuration with a gradually reducing diameter from the first region 17 to the end region 16, as illustrated in FIG. 4, due to the variation in radial stiffness.

FIG. 3 illustrates the stent 1 before deployment with no taper evident at the stent end 16. FIG. 4 illustrates the stent 1 after deployment with the taper evident at the stent end 16.

The variation in radial stiffness along part of the length of the stent 1 reduces the area of blood vessel wall which has low wall shear stress, reduces the possibility of recirculation, and reduces the risk of neointimal hyperplasia. Levels of mean wall shear stress below 0.4 Pa have been shown to have a pathogenic effect on endothelial cells which cover the inner surface of the arteries. Higher levels of wall shear stress, for example greater than 1.5 Pa, have been associated with a reduction in levels of in-stent restenosis.

An alternative arrangement of sudden expansion from a stent to a blood vessel may lead to poor performance in terms of wall shear. The invention addresses this problem by gradually changing the diameter of the stent 1 at the ends. By varying the radial stiffness of the stent 1 the invention ensures that good apposition of the stent 1 to the vessel wall is maintained. A number of approaches are possible to achieve the diameter increase at the stent ends in a gradual manner. The strut cross section may be reduced towards the stent ends, and/or the strut length may be increased towards the stent ends.

The radial stiffness is proportional to the strut width. As the strut width increases the radial force increases. The radial stiffness is inversely proportional to the strut length. As the strut length decreases the radial force increases.

No recirculation region occurs with the stent 1 with tapering radial stiffness. A recirculation region would arise at the proximal end of a non-tapered stent with constant radial stiffness due to the sudden area change at the proximal end.

Increasing the length of the tapered region reduces the surface area of wall shear stress below 0.4 Pa.

The stent 1 has the blended regions 3, 5 and is tapered. In this manner the levels of wall shear stress are significantly improved. The regions of low wall shear stress are associated with in-stent restonosis. Therefore increasing the wall shear stress reduces the levels of in-stent restonosis. The tapering is achieved by varying the radial stiffness at the proximal and distal ends of the stent 1.

The invention includes a taper on the intermediate sections 3, 5. The taper is achieved by changing the radial stiffness. The rate of expansion of the taper is constant over the overall taper length. In this case the expansion is from a 5 mm vessel to a 6 mm stented diameter.

The effect of the taper on the blended region wall shear stress is as follows.

By including the tapering section at the proximal end of the stent 1, the region of low wall shear stress below 0.4 Pa is reduced when compared with a sudden expansion into a helical stent which would result in a large region of low wall shear stress at the proximal end of the stent due to the sudden area change from the 5 mm to 6 mm blood vessel.

The surface area below 0.4 Pa may be used as a metric to evaluate the performance of a tapered stent. Increasing the length of the taper on the blended regions 3, 5 reduces the surface area of wall shear stress below 0.4 Pa.

The first four crowns 11 may have reducing strut width. The last crown 11 may have longer strut length, thus helping to achieve the desired low radial stiffness without reducing the strut width.

In use, the stent 1 is arranged in the collapsed delivery configuration with the central section 2, the first intermediate section 3, the first end section 4, the second intermediate section 5, and the second end section 6 all cylindrically shaped. When the stent 1 is outside of the blood vessel, the stent 1 has a constant diameter from the first region 17 to the end region 16, as illustrated in FIG. 3. The stent 1 is delivered through a blood vessel to the desired site of treatment. The stent 1 is then moved from the delivery configuration to the expanded deployment configuration to support at least part of an internal wall of the blood vessel. In the deployment configuration the central section 2 is helically shaped, and the first end section 4 and the second end section 6 are cylindrically shaped. After deployment of the stent 1 in the blood vessel, the stent 1 has a tapered configuration with a gradually reducing diameter from the first region 17 to the end region 16, as illustrated in FIG. 4, due to the variation in radial stiffness.

When the stent 1 is deployed in the blood vessel, the stent 1 exerts force on the blood vessel causing at least part of the longitudinal axis of the blood vessel to curve in three-dimensional space. In this manner the stent 1 acts to support at least part of the internal wall of the blood vessel curved in three-dimensional space. Blood flowing through the three-dimensional curved part of the blood vessel then undergoes a swirling action. The swirling flow of blood has been found to minimise thrombosis and platelet adhesion, and to minimise or prevent coverage of the stent 1 by ingrowth of intima. The flow pattern in the blood vessel including the swirling pattern induced by the non-planar geometry of the blood vessel operates to inhibit the development of vascular diseases such as thrombosis/atherosclerosis and intimal hyperplasia.

It will be appreciated that the shape of the stent may be varied.

Figure 9:
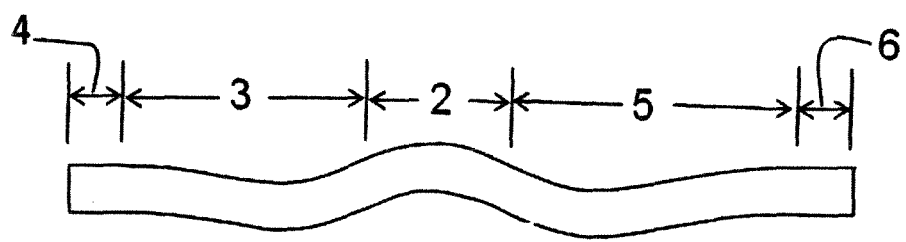
FIGS. 9 to 13 are side views of other stents according to the invention in the deployment configuration.

For example, as illustrated in FIG. 9, the central section 2 may be shorter in length than each of the intermediate sections 3, 5.

Figure 10:
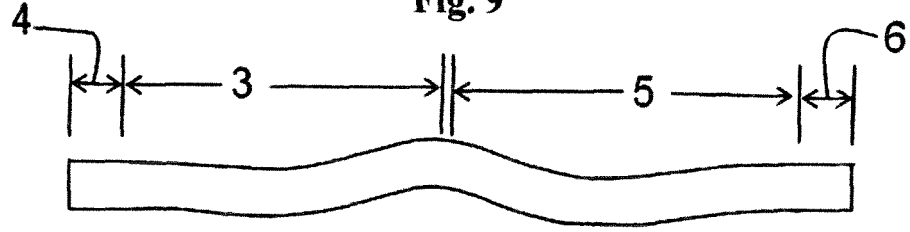

As illustrated in FIG. 10, the stent may comprise the first intermediate section 3, the first end section 4, the second intermediate section 5, and the second end section 6. In this case the stent does not include a central section.

Figure 11:
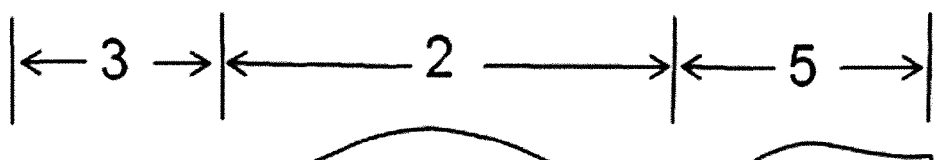

As illustrated in FIG. 11, the stent may comprise the central section 2, the first intermediate section 3, and the second intermediate section 5. In this case the stent does not include a first end section, or a second end section.

Figure 12:
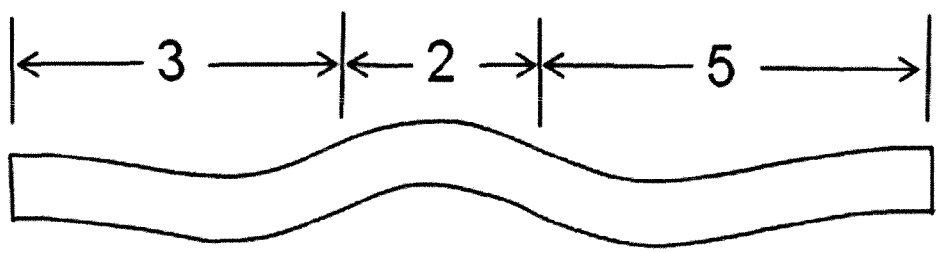

As illustrated in FIG. 12, the central section 2 may be shorter in length than each of the intermediate sections 3, 5.

Figure 13:
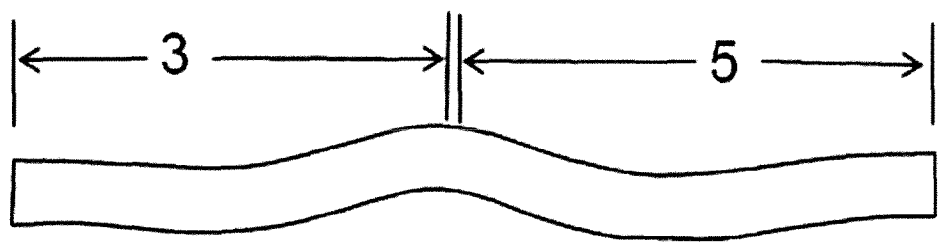

As illustrated in FIG. 13, the stent may comprise the first intermediate section 3, and the second intermediate section 5. In this case the stent does not include a central section, or a first end section, or a second end section.

Figure 14:
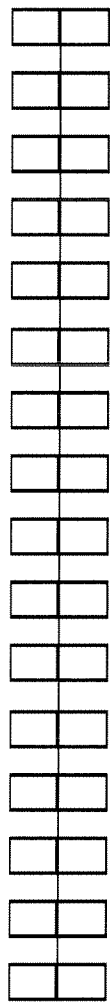
FIG. 14 is a side view of another stent according to the invention in the delivery configuration.
Figure 15:
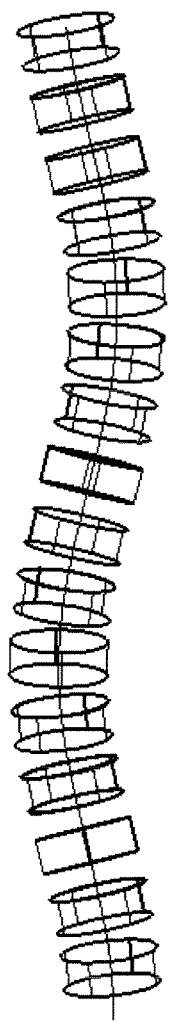
FIG. 15 is a side view of the stent of FIG. 14 in the deployment configuration.

It will be appreciated that in the deployment configuration the central section may have a piecewise helical shape, as illustrated in FIGS. 14 and 15. The stent may be formed of a series of short crown-shaped elements. Adjacent crowns are arranged in series and are linked by connector elements forming a tubular structure. Each crown is mostly cylindrical in shape having a straight centreline. The centreline of a straight stent is defined by a series of crown centrelines arranged in a co-linear fashion, as illustrated in FIG. 14. In certain embodiments of a three-dimensional stent, the crown centreline segments are no longer co-planar. In one such embodiment the stent centreline forms a piecewise linear three-dimensional curve. In another such embodiment the stent centreline is a series of discontinuous line segments, as illustrated in FIG. 15.

The central section may have an alternative shape, for example in the deployment configuration the central section may be substantially spiral shaped. Similarly the intermediate section may have an alternative shape, for example in the deployment configuration the intermediate section may be substantially spiral shaped.

Figure 16:
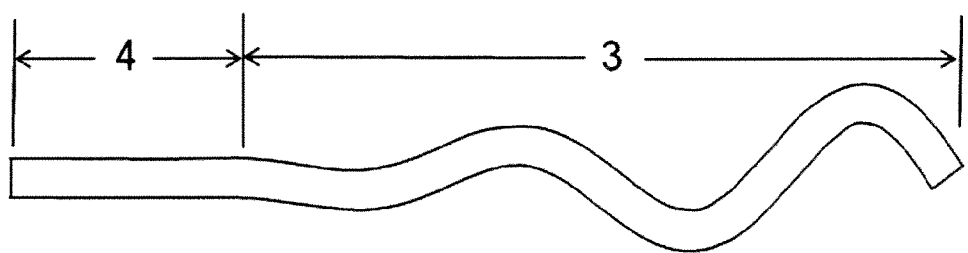
FIGS. 16 and 17 are side views of other stents according to the invention in the deployment configuration.
Figure 17:
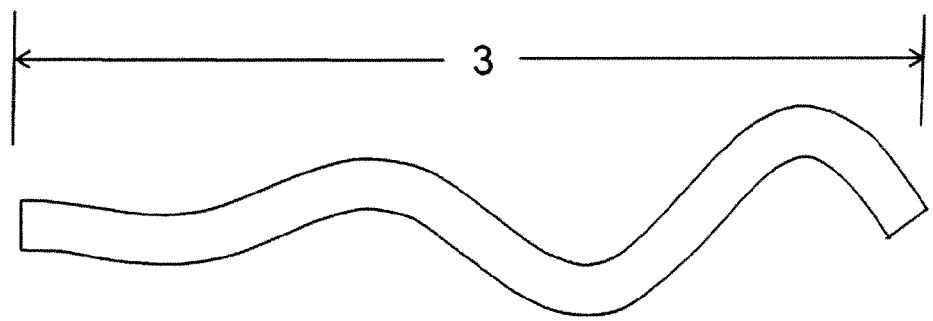

As illustrated in FIG. 16, the stent may comprise the first intermediate section 3, and the first end section 4. In this case the stent does not include a central section, or a second intermediate section, or a second end section. In the deployment configuration the first intermediate section 3 is substantially spiral shaped As illustrated in FIG. 17, the stent may comprise the first intermediate section 3 only. In this case the stent does not include a central section, or a first end section, or a second intermediate section, or a second end section. In the deployment configuration the first intermediate section 3 is substantially spiral shaped The invention is not limited to the embodiments hereinbefore described, with reference to the accompanying drawings, which may be varied in construction and detail.

The invention claimed is:

1. A stent suitable for deployment in a blood vessel to support at least part of an internal wall of the blood vessel, the stent being movable between a delivery configuration and a deployed configuration, the stent comprising a first region and two second regions, a radial stiffness of the first region being greater than a radial stiffness of each of the second regions wherein the stent has first and second ends and wherein one of the second regions is located at the first end of the stent, and the other one of the second regions is located at the second end of the stent;

wherein the stent comprises a plurality of annular elements, including at least first and second annular elements in the first region and at least one annular element in each of the second regions, the first and second annular elements in the first region being arranged longitudinally adjacent to each other and being connected together by at least one connecting element, wherein a longitudinal dimension of each of the first and second annular elements in the first region is less than a longitudinal dimension of the at least one annular element in each of the second regions, whereby the radial stiffness in each of the second regions is less than the radial stiffness in the first region due to the greater longitudinal dimension of the at least one annular element in each of the second regions than the longitudinal dimension of each of the first and second annular elements in the first region;

wherein the stent extends longitudinally and has a centreline;

wherein the stent has a first end section at one longitudinal end thereof and a second end section at an opposite longitudinal end thereof, and a section located between the first and second end sections;

wherein in the deployed configuration the centreline of the section of the stent located between the first and second end sections is curved in three-dimensional space; and wherein in the deployed configuration the centreline of the first end section is substantially co-linear with the centreline of the second end section.

2. A stent as claimed in claim 1 wherein the radial stiffness varies gradually from the first region towards at least one of the second regions.

3. A stent as claimed in claim 1 wherein a thickness of a stent wall in the first region is greater than a thickness of a stent wall in at least one of the second regions.

4. A stent as claimed in claim 1 wherein the connecting element extends from the first annular element to the second annular element in a non-straight configuration.

5. A stent as claimed in claim 4 wherein the connecting element extends from the first annular element to the second annular element in a substantially curved configuration.

6. A stent as claimed in claim 1 wherein the plurality of annular elements comprises a plurality of interconnected strut elements.

7. A stent as claimed in claim 6 wherein a length of a strut element in the first region is less than a length of a strut element in at least one of the second regions.

8. A stent as claimed in claim 6 wherein a width of the strut element in the first region is greater than a width of the strut element in at least one of the second regions.

9. A stent as claimed in claim 6 wherein a thickness of the strut element in the first region is greater than a thickness of the strut element in at least one of the second regions.

10. A stent as claimed in claim 6 wherein a first strut element is connected to a second strut element at a connection point.

11. A stent as claimed in claim 10 wherein the connecting element is connected to the annular element at the connection point.

12. A stent as claimed in claim 1 wherein in the deployed configuration the three-dimensionally curved section is substantially helically shaped.

13. A stent as claimed in claim 1 wherein in the deployed configuration the three-dimensionally curved section is substantially spiral shaped.

14. A stent as claimed in claim 1 wherein in the delivery configuration the longitudinal axis of the three-dimensionally curved section is substantially straight.

15. A stent as claimed in claim 14 wherein in the delivery configuration the three-dimensionally curved section is substantially cylindrically shaped.

16. A stent as claimed in claim 1, wherein the at least one connecting element extends from the first annular element to the second adjacent annular element in a curved "Z" or "S" shaped configuration.

17. A stent suitable for deployment in a blood vessel to support at least a part of an internal wall of the blood vessel, wherein the stent is movable between a delivery configuration and a deployed configuration, the stent comprising:

generally constant diameter between a first end and a second end thereof in the delivery configuration, and including a first region and two second regions, wherein the first region is located between the two second regions, wherein one second region is located at the first end of the stent and the other second region is located at the second end of the stent;

wherein a radial stiffness of the first region is greater than is a radial stiffness of each of the second regions;

wherein the stent comprises a plurality of annular elements including at least first and second annular elements located in the first region and at least one annular element located in each of the second regions, the first and second annular elements in the first region being arranged longitudinally adjacent to each other and being connected together by at least one connecting element, wherein a longitudinal dimension of each of the first and second annular elements in the first region is less than a longitudinal dimension of the at least one annular element in each of the second regions, whereby the radial stiffness in each of the second regions is less than the radial stiffness in the first region due to the greater longitudinal dimension of the at least one annular element in each of the second regions than the longitudinal dimension of each of the first and second annular elements in the first region;

wherein in the deployed configuration of the stent, a centreline of at least a section of the stent is curved in three-dimensional space; and wherein the stent is configured such that when it is in the deployed configuration and in a blood vessel, the diameter of the stent reduces toward at least one end.

18. A stent as claimed in claim 17 wherein the plurality of annular elements comprises a plurality of interconnected strut elements.

* * * * *

UNITED STATES PATENT AND TRADEMARK OFFICE
CERTIFICATE OF CORRECTION

| | |
|---|---|
| PATENT NO. | : 9,149,377 B2 |
| APPLICATION NO. | : 12/249389 |
| DATED | : October 6, 2015 |
| INVENTOR(S) | : Kevin Heraty et al. |

It is certified that error appears in the above-identified patent and that said Letters Patent is hereby corrected as shown below:

Claims

In Claim 17, column 10, line 12, "generally constant" should read "a tubular member having a".

Signed and Sealed this
Twelfth Day of July, 2016

Michelle K. Lee
*Director of the United States Patent and Trademark Office*